(12) United States Patent
Norfray

(10) Patent No.: US 8,131,337 B2
(45) Date of Patent: Mar. 6, 2012

(54) METHOD FOR MONITORING EARLY TREATMENT RESPONSE

(75) Inventor: Joseph F. Norfray, Glenview, IL (US)

(73) Assignee: Receptomon, LLC, Glenview, IL (US)

( * ) Notice: Subject to any disclaimer, the term of this patent is extended or adjusted under 35 U.S.C. 154(b) by 1209 days.

(21) Appl. No.: 11/397,877

(22) Filed: Apr. 4, 2006

(65) Prior Publication Data

US 2006/0222591 A1 Oct. 5, 2006

Related U.S. Application Data

(60) Provisional application No. 60/668,304, filed on Apr. 5, 2005, provisional application No. 60/703,597, filed on Jul. 29, 2005.

(51) Int. Cl.
*A61B 5/05* (2006.01)
(52) U.S. Cl. .......... 600/410; 564/210; 424/400; 424/9.5
(58) Field of Classification Search .................. 600/410; 564/293; 424/400, 9.5, 9.6, 9.7, 9.8
See application file for complete search history.

(56) References Cited

U.S. PATENT DOCUMENTS

| | | | |
|---|---|---|---|
| 4,354,499 A | 10/1982 | Damadian | |
| 4,411,270 A | 10/1983 | Damadian | |
| RE32,619 E | 3/1988 | Damadian | |
| RE32,689 E | 6/1988 | Damadian | |
| 4,843,321 A | 6/1989 | Sotak | |
| 4,962,357 A | 10/1990 | Sotak | |
| 5,111,819 A | 5/1992 | Hurd | |
| 5,200,345 A | 4/1993 | Young | |
| 5,220,302 A * | 6/1993 | Nunnally et al. ............. | 335/301 |
| 5,498,421 A | 3/1996 | Grinstaff et al. | |
| 5,578,921 A | 11/1996 | Morrell | |
| 5,585,118 A | 12/1996 | Stoll | |
| 5,617,861 A | 4/1997 | Ross et al. | |
| 5,887,588 A | 3/1999 | Usenius et al. | |
| 5,903,149 A | 5/1999 | Gonen et al. | |
| 6,046,589 A | 4/2000 | Lamerichs et al. | |
| 6,181,134 B1 | 1/2001 | Wald | |
| 6,280,383 B1 | 8/2001 | Damadian | |
| 6,347,239 B1 | 2/2002 | Arnold et al. | |
| 6,400,150 B1 | 6/2002 | Liu et al. | |
| 6,617,169 B2 | 9/2003 | Ke et al. | |
| 6,630,125 B2 | 10/2003 | DeGrado et al. | |
| 6,639,405 B2 | 10/2003 | Liu et al. | |
| 6,681,132 B1 | 1/2004 | Katz et al. | |
| 6,708,053 B1 | 3/2004 | Brooks et al. | |
| 6,756,063 B2 | 6/2004 | Kiss | |
| 6,819,952 B2 | 11/2004 | Pfefferbaum et al. | |
| 6,838,877 B2 | 1/2005 | Heid et al. | |
| 7,289,840 B2 | 10/2007 | Norfray | |
| 7,572,448 B2 | 8/2009 | Thorpe et al. | |
| 7,622,102 B2 | 11/2009 | Norfray | |
| 7,771,706 B2 | 8/2010 | Norfray | |
| 2001/0003423 A1 | 6/2001 | Wald | |
| 2002/0061279 A1* | 5/2002 | DeGrado et al. ............. | 424/1.89 |
| 2002/0142367 A1 | 10/2002 | Ke et al. | |
| 2002/0173713 A1 | 11/2002 | Pfefferbaum et al. | |
| 2003/0028093 A1 | 2/2003 | Ke et al. | |
| 2003/0199751 A1 | 10/2003 | Gonzalez et al. | |
| 2003/0208120 A1 | 11/2003 | Thomas et al. | |
| 2004/0092809 A1 | 5/2004 | DeCharms | |
| 2005/0031620 A1 | 2/2005 | Thorpe et al. | |
| 2005/0107683 A1 | 5/2005 | Mountford et al. | |
| 2006/0035945 A1 | 2/2006 | Attardo et al. | |
| 2006/0064003 A1 | 3/2006 | Norfray | |
| 2006/0177377 A1 | 8/2006 | Norfray | |
| 2006/0177378 A1 | 8/2006 | Norfray | |
| 2007/0128114 A1 | 6/2007 | Norfray | |
| 2007/0218006 A1 | 9/2007 | Norfray | |

FOREIGN PATENT DOCUMENTS

| | | |
|---|---|---|
| WO | WO 2006/036288 A2 | 4/2006 |
| WO | WO 2006/086159 A2 | 8/2006 |
| WO | WO 2006/107950 A2 | 10/2006 |

OTHER PUBLICATIONS

Daly et al., Phospholipid Metabolism in Cancer Cells Monitored by P31 NMR Spectroscopy, Nov. 5, 1987, The Journal of Biological Chemistry, 262(31), pp. 14875-14878.*
U.S. Appl. No. 11/053,059, filed Feb. 8, 2005, Norfray.
U.S. Appl. No. 11/193,037, filed Jul. 29, 2005, Norfray.
Balkwill et al., *The Lancet*, 357, 539-545 (2001).
Bianco et al., *British Journal of Cancer*, 89, (Suppl. 2) (2003) S25-S35 Abstract.
Blackledge et al., *British Journal of Cancer*, 90, 566-572 (2004).
Bluml et al., *Magn. Reson. Med.*, 42, 643-654 (1999).
Boyer, *British Journal of Cancer*, 89, (Suppl. 2) (2003) S25-S35 Abstract.
Bunz et al., *The Journal of Clinical Investigation*, 104(3), 263-269 (Aug. 1999).
Cappuzzo et al. *I British Journal of Cancer*, 89, (Suppl. 2) (2003) S25-S35 Abstract.
Cappuzzo et al. *II British Journal of Cancer*, 89, (Suppl. 2) (2003) S25-S35 Abstract.
Chioni et al., *British Journal of Cancer*, 89, (Suppl. 2) (2003) S25-S35 Abstract.
Colman, *Semin. Thromb. Hemost.*, 30(1), 45-61 (2004).
Cortes-Funes et al., *British Journal of Cancer*, 89, (Suppl. 2) (2003) S25-S35 Abstract.

(Continued)

*Primary Examiner* — Brian Casler
*Assistant Examiner* — Nasir Shahrestani
(74) *Attorney, Agent, or Firm* — Leydig, Voit & Mayer, Ltd.

(57) ABSTRACT

Disclosed is a method for monitoring early treatment response of a cancer treatment comprising measuring by magnetic resonance spectroscopy (MRS), for example, proton MRS, the amount of Choline present in the endomembranes of the cancerous tissue before and after treatment; the treatment comprises administration of a cytotoxic therapy, whereby a decrease in the amount of Choline after treatment is indicative of a positive response. The decrease in the amount of Choline represents the decrease in the internal cell membrane as a result of down regulation of the organelles and their secretory granules and their transport vesicles. Disclosed also is a method for determining effectiveness of a cytotoxic treatment of cancer. In addition, a method for monitoring protein translation related to the cytotoxic treatment of cancer is disclosed.

30 Claims, No Drawings

OTHER PUBLICATIONS

Danielsen et al., *Magnetic Resonance Spectroscopy Diagnosis of Neurological Diseases*, Marcel Dekker, Inc. Ch.3: The clinical significance of metabolites, 23-43 (1999).
de Braud et al., *British Journal of Cancer*, 89, (Suppl. 2) (2003) S25-S35 Abstract.
DeClerck et al., *Am. J. Pathol.*, 164(4), 1131-1139 (Apr. 2004).
de la Cruz et al., *I British Journal of Cancer*, 89, (Suppl. 2) (2003) S25-S35 Abstract.
de la Cruz et al., *II British Journal of Cancer*, 89, (Suppl. 2) (2003) S25-S35 Abstract.
de Leeuw et al., *British Journal of Cancer*, 89, (Suppl. 2) (2003) S25-S35 Abstract.
Diaz-Canton, *British Journal of Cancer*, 89, (Suppl. 2) (2003) S25-S35 Abstract.
Dieriks et al., *British Journal of Cancer*, 89, (Suppl. 2) (2003) S25-S35 Abstract.
Eliason et al., *Current Drug Targets*, 5, 383-388 (2004).
Engelse et al., *Semin. Thromb. Hemost.*, 30(1), 71-82 (2004).
Erlich, *IDrugs*, 6(4), 331-333 (2003).
Evelhoch, *Cancer Research*, 47, 3396-3401 (Jul. 1, 1987).
Fernandez et al., *Semin. Thromb. Hemost.*, 30(1), 31-44 (2004).
Fisher et al., *Neuroimg. Clin. N. Am.* 12, 477-499 (2002).
Fujimoto et al., "A new immunological parameter predicting the efficacy of cancer therapy", Editorial, *Annals of Cancer Research and Therapy*, 7(2) (Title Only).
Fujimoto et al., *The 11$^{th}$ International Congress of Immunology* (2001) (Abstract).
Fulham et al., *Radiology*, 185, 675-686 (1992).
Gelibter et al., *British Journal of Cancer*, 89, (Suppl. 2) (2003) S25-S35 Abstract.
Gervais et al., *British Journal of Cancer*, 89, (Suppl. 2) (2003) S25-S35 Abstract.
Griffiths et al. *The Lancet*, 1435-1436, (Jun. 25, 1983).
Harrigan, *Neurosurgery*, 53(3), 639-660 (2003).
Jin et al., *Br. J. Cancer*, 90, 561-565 (2004).
Katz et al., *British Journal of Cancer*, 89 (Suppl. 2) (2003) S25-S35 Abstract.
Kowalski et al., *British Journal of Cancer*, 89, (Suppl. 2) (2003) S25-S35 Abstract.
Kreis et al., *J. Magnetic Resonance Series B*, 102, 9-19 (1993).
Lynch et al., *New England Journal of Medicine*, 350(21), 2129-2139 (May 20, 2004).
Maione et al., *British Journal of Cancer*, 89, (Suppl. 2) (2003) S25-S35 Abstract.
Mancuso et al., *British Journal of Cancer*, 89, (Suppl. 2) (2003) S25-S35 Abstract.
Martin-Algarra et al., *British Journal of Cancer*, 89, (Suppl. 2) (2003) S25-S35 Abstract.
Martinez, *British Journal of Cancer*, 89, (Suppl. 2) (2003) S25-S35 Abstract.
Matsumoto et al., *Jpn. J. Clin. Oncol*, 34(3), 124-130 (2004).
Negendank, *NMR in Biomedicine*, 5, 303-324 (1992).
Negendank, *Radiology*, 185, 875-883 (1992).
Nie et al., *Semin, Thromb. Hemost.* 30(1), 119-125 (2004).
Norfray et al., *AJR*, 173, 119-125, (Jul. 1999).
Norfray et al., *AJR*, 182(3), 3-13, (Jan. 2004).
Norfray et al., *Journal of Computer Assisted Tomography*, 23(6), 994-1003 (1999).
Norfray, et al., *Pediatric Neurosurgery*, 4$^{th}$ Edition, Ch. 110, McLone (ed), 1189-1203 W.B. Sunders Co. (2001).
Norfray et al., *ARRS Annual Meeting*, (May 4-9, 2003) 1 page Abstract.
Petersen et al., *British Journal of Cancer*, 89, (Suppl. 2) (2003) S25-S35 Abstract.
Petruzelka et al. *British Journal of Cancer*, 89, (Suppl. 2) (2003) S25-S35 Abstract.
Podo, *NMR in Biomedicine*, 12, 413-429 (1999).
Ranson et al., *Journal of Clinical Oncology*, 20(9), 2240-2250 (May 1, 2002).
Razis et al., *British Journal of Cancer*, 89, (Suppl. 2) (2003) S25-S35 Abstract.
Reck et al., *British Journal of Cancer*, 89, (Suppl. 2) (2003) S25-S35 Abstract.
Ross et al. *Arch. Surg.*, 122, 1464-1469 (Dec. 1987).
Ross, *The Biochemistry of Living Tissues: Examination by MRS*, 215-219 (1992).
Ross et al., *Magnetic Resonance Quarterly*, 10, 191-247 (1994).
Ross et al., *Journal of Computer Assisted Tomography*, 13(2), 189-193, (Mar./Apr. 1989).
Ross et al., *The Lancet*, 641-646 (Mar. 1984).
Ruiz-Cabello, *NMR in Biomedicine*, 5, 226-233 (1992).
Schwarz et al., *The British Journal of Radiology*, 75, 959-966 (Dec. 2002).
Schmitt et al., *Journal of Pathology*, 187, 127-137 (1999).
Sierko et al., *Semin. Thromb. Hemost.*, 30(1), 95-108 (2004).
Stein et al., *British Journal of Cancer*, 89, (Suppl. 2) (2003) S25-S35 Abstract.
Tang et al., *Semin. Thromb. Hemost.* 30, 109-117 (2004).
van der Kamp et al., *British Journal of Cancer*, 89, (Suppl. 2) (2003) S25-S35 Abstract.
van Zandwijk, *I British Journal of Cancer*, 89, (Suppl. 2) (2003) S25-S35 Abstract.
van Zandwijk, *II British Journal of Cancer*, 89, (Suppl. 2) (2003) S25-S35 Abstract.
Vincent, *British Journal of Cancer*, 89, (Suppl. 2) (2003) S25-S35 Abstract.
Wojtukiewicz et al., *Semin. Thromb. Hemost.* 30(1), 145-156 (2004).
Yu et al., *Semin. Thromb. Hemost.* 30(1), 21-30 (2004).
Becker et al., "Intracellular Compartments: The endoplasmic reticulum, Golgi Complex, Lysosomes, and Peroxisomes", *The World of the Cell, Third Edition*, The Benjamin/Cummings Publishing Company, Ch. 9, pp. 229-270 (1996).
Daly et al., "Phospholipid Metabolism in Cancer Cells Monitored by $^{31}$P NMR Spectroscopy", *The Journal of Biological Chemistry*, 262(31): 14875-14878 (Nov. 5, 1987).
Dzik-Jurasz, A., "Angiogenesis Imaging in Man: A Personal View From the Pharmaceutical Industry," *The British Journal of Radiology*, Special Issue 2003, pp. S81-S82 (2003).
Encyclopaedia Britannica, "Cells: Their Structures and Functions", *The New Encyclopaedia Britannica*, V. 15, Macropaedia, 15$^{th}$ edition, pp. 565-593 (1994).
Farhadi, et al., "Combined Inhibition of Vascular Endothelial Growth Factor and Platelet-Derived Growth Factor Signaling: Effects on the Angiogenesis, Microcirculation, and Growth of Orthotopic Malignant Gliomas", *Journal of Neurosurgery*, 102:363-370 (Feb. 2005).
Fukuoka et al., "Multi-Institutional Randomized Phase II Trial of Gefitinib for Previously Treated Patients with Advanced Non-Small-Cell Lung Cancer", *Journal of Clinical Oncology*, vol. 21, No. 12 Jun. 15, 2003: pp. 2237-2246 DOI: 10.1200/JCO.2003.10.038.
Fuller et al., "Organelles and Vesicle Traffic," *Molecular Basis of Medical Cell Biology* (a Lange medical book), Ch. 4, pp. 67-92 (1998).
Galbraith, S.M., "Antivascular Cancer Treatments: Imaging Biomarkers in Pharmaceutical Drug Development", *The British Journal of Radiology*, 76 (2003), S83-S86 DOI: 10,1259/bjr/15255885.
Kauppinen, Risto A., "Monitoring Cytotoxic Tumour Treatment Response by Diffusion Magnetic Resonance Imaging and Proton Spectroscopy," *NMR Biomedicine*, 2002:15:6-17; DOI:10.1002/nbm.742.
Laird et al., *Cancer Research*, 2000, vol. 60, pp. 4152-4160.
Leach et al., "The Assessment of Antiangiogenic and Antivascular Therapies in Early-Stage Clinical Trials Using Magnetic Resonance Imaging; Issues and Recommendations," *British Journal of Cancer* (2005) 92 (9), pp. 1599-1610.
Mukherji et al., *AJNR Am. J. Neuroradio.*, 1996, vol. 17, pp. 1485-1490.
Nakagami et al., "Increased Choline Kinase Activity and Elevated Phosphocholine Levels in Human Colon Cancer," *Jpn. J. Cancer Res*, 90, 419-424, Apr. 1999.
Pollard, Thomas D., "Programmed Cell Death," *Cell Biology*, Elsevier, Inc., Ch. 49, pp. 767-782 (2004); ISBN 1-4160-2388-7.
Taga et al., Abstract, *International Journal of Cancer* 98(5), 690-697 (Apr. 10, 2002).

Yamanaka et al., Abstract "Gene Therapy of Brain Tumor with Endostatin", *Drugs Today*, 40(11), 931-914 (Nov. 2004).

Bernales et al., Autophagy counterbalances endoplasmic reticulum expansion during the unfolded protein response, *PLoS Biology*, 4 (12): (e423) 2311-2324 (Dec. 2006).

Blankenberg et al., Detection of apoptotic cell death by proton nuclear magnetic resonance spectroscopy, *Blood*, 87: 1951-1956 (1996).

Blankenberg et al., Quantitative analysis of apoptotic cell death using proton nuclear magnetic resonance spectroscopy, *Blood*, 89 (10): 3778-3786 (May 15, 1997).

Bursch et al., Programmed cell death (PCD): apoptosis, autophagic PCD, or others?, *Annals N.Y. Academy of Science*, 926: 1-13 (Dec. 2000).

Clemens et al., Translation initiation factor modifications and the regulation of protein synthesis in apoptotic cells, *Cell Death and Differentiation*, 7: 603-615 (2000).

European Patent Office, Supplementary European search report for cognate European Application No. 06733897.0, mailed Feb. 20, 2009.

European Patent Office, Communication pursuant to Article 94(3) EPC relating to cognate European Application No. 06733897.0, mailed Jun. 18, 2009.

Ferreira et al., Apoptosis: target of cancer therapy, *Clinical Cancer Research*, 8: 2024-2034 (Jul. 2002).

Lindskog et al., Predicting resistance or response to chemotherapy by proton magnetic resonance spectroscopy in neuroblastoma, *Journal of the National Cancer Institute*, 96 (19): 1457-1466 (2004).

Maiuri et al., Self-eating and self-killing: crosstalk between autophagy and apoptosis, *Nature Reviews/Molecular Cell Biology*, 8: 741-752 (Sep. 2007).

Meisamy et al., Neoadjuvant chemotherapy of locally advanced breast cancer: predicting response with in vivo $^1$H MR spectroscopy—a pilot study at 4 $T^1$, *Radiology*, 233: 424-431 (2004).

Mohamad et al., Mitochondrial apoptotic pathways, *Biocell*, 29(2): 149-161 (2005).

Schmitt et al., Apoptosis and therapy, *Journal of Pathology*, 187: 127-137 (1999).

Scott et al., $^{13}$C-NMR investigation of protein synthesis during apoptosis in human leukemic cell lines, *Journal of Cellular Physiology*, 181: 147-152 (1999).

Shaffer et al., XBP1, downstream of blimp-1, expands the secretory apparatus and other organelles, and increases protein synthesis in plasma cell differentiation, *Immunity*, 21: 81-93 (Jul. 2004).

European Patent Office, extended European Search Report relative to cognate European Patent Application No. 05778030.6, mailed Mar. 3, 2010.

European Patent Office, Office Communication relative to cognate European Patent Application No. 05778030.6, mailed Jun. 14, 2010.

European Patent Office, extended European Search Report relative to related European Patent Application No. 06740479.8, mailed Sep. 17, 2009.

European Patent Office, Office Communication relative to related European Patent Application No. 06740479.8, mailed Dec. 8, 2009.

European Patent Office, Office Communication relative to related European Patent Application No. 06740479.8, mailed Apr. 18, 2011.

Gerdes, J. et al., Production of a mouse monoclonal antibody reactive with a human nuclear antigen associated with cell proliferation, *Int. Journal Cancer*, 31: 13-20, 1983.

Indian Patent Office, Examination Report relative to related Indian Patent Application No. 1358/MUMNP/2007, mailed Nov. 23, 2010.

International Searching Authority, "International search report" and "Written opinion of the International Searching Authority," for related International Application No. PCT/US05/27060, mailed Jan. 24, 2007.

International Searching Authority, "International search report" and "Written opinion of the International Searching Authority," for related International Application No. PCT/US06/02675, mailed Sep. 21, 2006.

Neeman, M. et al., Early estrogen-induced metabolic changes and their inhibition by actinomycin D and cycloheximide in human breast cancer cells: $^{31}$P and $^{13}$C NMR studies, *Proc. Natl. Acad. Sci. USA*, 86: 5585-5589, Jul. 1989.

Schneider-Poetsch, T. et al., Inhibition of eukaryotic translation elongation by cycloheximide and lactimidomycin, *Nat Chem Biol*, Mar. 2010, 6(3): 209-217.

Sobell, Henry M., Actinomycin and DNA transcription, *Proc. Natl. Acad. Sci. USA*, Aug. 1985, 82: 5328-5331.

USPTO, Office Action relative to related U.S. Appl. No. 10/946,741 (now U.S. Patent No. 7,289,840), mailed Jun. 14, 2006.

USPTO, Office Action relative to related U.S. Appl. No. 10/946,741 (now U.S. Patent No. 7,289,840), mailed Jan. 11, 2007.

USPTO, Office Action relative to related U.S. Appl. No. 11/053,059 (now U.S. Patent No. 7,622,102), mailed Jun. 15, 2009.

USPTO, Office Action relative to related U.S. Appl. No. 11/193,037 (now abandoned), mailed Jan. 26, 2007.

USPTO, Office Action relative to related U.S. Appl. No. 11/193,037 (now abandoned), mailed Sep. 11, 2007.

USPTO, Office Action relative to related U.S. Appl. No. 11/622,321 (now U.S. patent No. 7,771,706), mailed Sep. 14, 2009.

USPTO, Office Action relative to related U.S. Appl. No. 11/622,321 (now U.S. patent No. 7,771,706), mailed Mar. 1, 2010.

USPTO, Office Action relative to related U.S. Appl. No. 11/576,198, mailed Oct. 15, 2010.

USPTO, Office Action relative to related U.S. Appl. No. 11/576,198, mailed Mar. 31, 2011.

USPTO, Office Action relative to related U.S. Appl. No. 11/576,198, mailed Jul. 14, 2011.

Wojtukiewicz, M. et al., Contribution of the hemostatic system to angiogenesis in cancer, *Semin. Thrombosis. Hemost.*, 30(1): 5-20, Nov. 1, 2004.

International Searching Authority; International Search Report and Written Opinion relative to International Application No. PCT/US06/012469 mailed Mar. 13, 2007.

* cited by examiner

METHOD FOR MONITORING EARLY TREATMENT RESPONSE

CROSS-REFERENCE TO RELATED APPLICATIONS

This patent application claims the benefit of U.S. Provisional Patent Application No. 60/668,304 filed Apr. 5, 2005 and U.S. Provisional Patent Application No. 60/703,597 filed Jul. 29, 2005, disclosures of which are incorporated by reference.

FIELD OF THE INVENTION

This invention pertains to a method for monitoring early response to cancer treatment, particularly in cytotoxic treatment involving radiation and chemotherapy, each alone or in combination. The method involves the use of Magnetic Resonance Spectroscopy (MRS).

BACKGROUND OF THE INVENTION

Some of the common approaches to cancer treatment include surgery, radiation therapy, and chemotherapy. Radiation therapy and chemotherapy are effective if they are capable of killing the tumor cells; i.e., when they act as cytotoxic agents. Typically, the response to radiation therapy or chemotherapy is monitored by magnetic resonance imaging (MRI) of the tumor, wherein a decrease in tumor size is indicative of positive response to treatment.

Cytotoxic therapies rely on disrupting the DNA and RNA of malignant cells. Radiation creates DNA strand breaks and aberrations. Examples of lethal aberrations are the ring and dicentric chromosomal aberrations, and the anaphase bridge chromatid aberration. Hall, E. J., Ch 2 in *Radiobiology for the Radiologist*, $5^{th}$ ed., Lippincott, Williams and Wilkins (2000). Cytotoxic agents or drugs generally alter DNA and RNA synthesis or functions, e.g., forming cross links between DNA strands (alkylating agents and platinum analogs); inhibiting DNA-dependent RNA polymerase (streptomycin drugs); blocking production of mitotic spindles (vinca alkaloids); and preventing disassociation of drug treated spindles (taxans). Hall, E. J., Ch 27, supra.

Cytotoxic agents induce apoptosis, a programmed cell death. Apoptosis is under the control of two signaling pathways. One pathway utilizes "death receptors" on the cancer cell membrane. Fas and tumor necrosis factor (TNF) receptors can be activated by cytotoxic drugs, such as adriamycin, forming caspase-8 thereby initiaing a protease cascade that cleaves cellular targets and results in apoptosis cell death. The second pathway is initiated by cellular stress, such as DNA damage from either radiation or chemotherapeutic agents. The DNA strand breaks are sensed by kinases that activate p53 (a tumor suppressor protein) resulting in the bax gene releasing cytochrome c from the mitochondria. Cytochrome c activates caspase-9 and downstream caspases causing apoptosis. Apoptosis links programmed cell death to DNA damage. Schmitt, C. A., et al., *J. Path.* 187, 127-137 (1999).

Unfortunately, tumors can be resistant to a class of chemotherapeutic agents, or develop resistance during the prolong exposure to a cytotoxic drug. Untreated tumors may have a mutation in p53, a tumor suppressor protein, preventing the release of cytochrome c from the mitochondria and thereby blocking apoptosis. Schmitt, et al., supra, and Bunz, F., et al., *J. Clin. Invest.* 104, 263-269 (1999). Drug resistance may develop during treatment by up-regulating the multiple drug resistance (mdr) gene that extrudes the drug out of the cell. Drug resistance may also develop the malignant cells increase intraceullular glutathione. Hall, E. J., Ch 27, supra.

Radiation resistance develops in hypoxic tumors because some DNA strand breaks are repaired. Radiation sensitivity is maintained in oxygenated tumors with oxygen forming peroxides that react with the DNA strand breaks preventing their repair. Hall, E. J., Ch 6 supra.

Cytotoxic resistance is now monitored by obtaining sequential contrast CT/MR studies at 3-12 month intervals. Resistance to treatment is identified by an increase in tumor size and an increase in enhancement (angiogenesis) of the tumor following the treatment. Therapeutic response is documented by decrease in tumor size and decrease in tumor enhancement. The decrease in size documents apoptosis with loss of cellularity. In many cases, a detectable change in tumor size is observed only after a significant long period of time, for example after treatment for a period of 3 months or more. Such long periods of time could be harmful to the patient for during this long period of time, tumor cells could multiply and/or metastasize, and lead to worsening the patient's condition.

The foregoing shows that there exists a need for a method where an early cytotoxic treatment response can be monitored. Accordingly, the present invention provides such a method. This and other advantages of the invention, as well as additional inventive features, will be apparent from the description of the invention provided herein.

BRIEF SUMMARY OF THE INVENTION

The invention provides a method for monitoring early treatment response of a cancer treatment comprising measuring by MRS, the amount of Choline present in the cancerous tissue, particularly in the internal cell membranes or endomembranes, before and after cytotoxic treatment; the treatment comprises radiation and/or chemotherapy, whereby a decrease in the amount of Choline after treatment is indicative of a positive response. In accordance with the invention, diagnosed cancers can be monitored by following cell membrane metabolism utilizing the Choline peak on $^1$H MR spectroscopy. The Choline peak represents the visible mobile Choline forming the plasma and organelle cell membranes. A decrease in the Choline identifies treatment response; an increase in the Choline peak identifies treatment failure.

The present invention provides one or more of several advantages, for example, the amount of Choline changes prior to classical imaging findings, and the MRS peak corresponding to Choline changes with a cytotoxic treatment based on radiation and/or chemotherapy. The present invention offers the combined advantages of MRI and MRS and provides a method to monitor early treatment response. The present invention also provides a method for monitoring cancer treatment. Further, the present invention also provides for a method for monitoring protein translation comprising administering an amount of the molecule or radiation to an animal having a cancerous tissue and measuring, by Magnetic Resonance Spectroscopy, the amount of Choline present in the endomembranes of the cancerous tissue before and after administering the molecule or radiation.

DETAILED DESCRIPTION OF THE INVENTION

The present invention is predicated on monitoring changes in the amount of one or more metabolites occurring in an internal cell membrane (endomembrane), for example, changes induced by the down regulation of one or more of the intracellular organelles and their secretory granules and transport vesicles. The internal cell membranes, which constitute nearly 90% of the total cell membranes, form the membranes of the nucleus, the mitochondria, the lysosomes, the peroxisomes, the endoplasmic reticulums, the Golgi apparatus, the secretory granules, and the transport vesicles. Cytotoxic agents down-regulate the intracellular organelles and their secretory granules and transport vesicles.

Following the endomembranes (intracellular organelles) correlates with Francis Crick's "Central Dogma of Molecular Biology". The central dogma involves DNA replication, transcription of information carried by DNA into the form of RNA, and translation of the information encoded in the RNA into proteins. Genetic alterations in tumors amplify the protein synthesis utilizes intracellular organelles, subcellular membrane-bounded compartments. The organelles include the nucleus, endoplasmic reticulum (ER), Golgi complex (GC), lyosomes, peroxisomes, and mitochondria. Protein synthesis is initiated in the nucleus by transcription of the appropriate DNA genes to form messenger, ribosomal and transfer RNA. Ribosomes are the "work benches" of protein synthesis linking amino acids into a polypeptide. Ribosomes adhere to the ER forming the rough ER (rER). The polypeptides enter rER for processing. Following protein processing in the rER, the proteins are packaged into transport vesicle and moved to the GC where further protein processing takes place. Other transport vesicles are generated to carry the proteins between the cisternae of the Golgi stack. Lysosomes are derived from cell membranes of the rER and GC and contain digestive enzymes needed to re-cycle membranes and proteins. The peroxisomes and mitochondria are multiplied to handle the increased production of hydrogen peroxide, and the increased demand for energy in protein synthesis. Secretory granules package and move the completed proteins from the Golgi complex to the plasma membrane where the proteins are either bound or secreted. While the cell membranes for the transport vesicles and secretory granules are generated by budding off the rER and GC cell membranes, the cell membranes for peroxisomes and mitochondria are generated by division of pre-existing peroxisomes and mitochondria. The continued budding of vesicles and granules off the rER and GC requires continued regeneration of rER and GC cell membranes. Therefore, in cancer, the uncontrolled protein synthesis is coupled to the increase in the intracellular cell membranes.

Following the changes in the endomembranes (organelle membranes) by MRS has several advantages over following apoptosis (loss of cellularity) by MRI. The changes in the total choline peak (MRS) occur before changes in size and enhancement (MRI) Norfray, J. F., et al., supra. MRS allows earlier determination of sensitivity or resistance to cytotoxic drugs than MRI. Norfray, J. F., et al., supra. The earlier changes seen by MRS are related to interruption of protein synthesis (translation) occurring within the organelles. The later changes seen by MRI are related to downstream programmed cell death (apoptosis) occurring with loss of tumor cells.

Accordingly, the present invention provides a method for monitoring early treatment response of a cancer treatment comprising measuring, by Magnetic Resonance Spectroscopy (MRS), the amount of Choline present in the endomembranes of the cancerous tissue before and after treatment; the treatment comprises administration of a cytotoxic agents, whereby a decrease in the amount of Choline after treatment is indicative of a positive response. MRS can be based on the resonance of any suitable nuclei; for example, nuclei selected from the group consisting of $^{31}P$, $^{1}H$, $^{13}C$, and $^{23}Na$, and any combination thereof, preferably, $^{1}H$.

The choline peak frequency is amplified during $^{1}H$ MRS, thereby becoming a valuable marker for cell membranes. $^{1}H$ MRS amplifies the Choline peak frequency, 10,000 times by removing the hydrogen signal from water leaving the hydrogen signal from detectable metabolites, including Choline. The choline signal is amplified another-nine-fold with the choline containing nine hydrogens per molecule (as trimethylamines or trimethylammonium salts). Further amplification occurs from the endomembranes that constitute 90% of the cell membranes, while the plasma membranes equal the remaining 10%.

The present invention also provides for a method for monitoring protein translation comprising administering an amount of the molecule or radiation to an animal having a cancerous tissue and measuring, by Magnetic Resonance Spectroscopy, the amount of Choline present in the endomembranes of the cancerous tissue before and after administering the molecule or radiation. The present invention can be used for monitoring protein translation. Choline visualizes cellular membranes. The quantity of choline directly correlates with the amount of intracellular organelles and intracellular organelles make up 90% of cell membranes. Some organelles, such as rER, are the site of protein synthesis. Some of the proteins synthesized in the cell's organelles are inserted into cellular membranes, while other proteins synthesized in the cell's organelles are secreted as part of a coordinated cellular process. An increase in protein synthesis increases mass of these organelles and a decrease in protein synthesis decreases the mass of these organelles. Thus, the cellular Choline level also reflects cellular protein synthesis. Accordingly, drugs up-regulating or down-regulating protein translation can be monitored by following an increase in Choline (resulting from an increase in organelles). Therefore, the current invention can monitor early treatment response by quantifying Choline of intracellular organelles linked to protein synthesis (translation). Further, the effect of drugs that can interrupt or up-regulate DNA replication (which requires protein translation) or RNA transcription (which results in protein translation), can be monitored by the current invention with protein translation visualized by decreases or increases in Choline.

The term "Choline" herein is used to denote choline $((CH_3)_3N^+CH_2CH_2OH)$, a derivative of choline, or a combination of choline and/or one or more derivatives of choline. Examples of choline derivatives include lysophosphatidylcholine, or glycerophosphocholine, phosphomonoesters of choline (e.g., phosphocholine), phosphodiesters of choline (e.g., phosphatidylcholine), sphingomyelin, phosphoethanolamine, glycerophosphoethanolamine, or any combination thereof. In an embodiment of the invention, the term "Choline" represents the sum of choline and all choline derivatives (or total choline), for example, the sum of choline and phosphocholine. Phosphoserine and glycerophosphoserine also can be monitored Ruiz-Cabello, J. et al., *NMR in Biomedicine*, 5, 223-233 (1992); Podo, F., *NMR in Biomedicine*, 12, 413-439 (1999); and Blüms, S. et al., *Magn. Reson. Med.*, 42, 643-654 (1999).

The amount of Choline can be measured by MRS in any suitable manner. For example, the amount of Choline can be measured by measuring the height of a peak or peaks corresponding to Choline. In another embodiment, the amount of Choline can be measured by measuring the area under a peak or peaks corresponding to Choline. In yet another embodiment, the amount of Choline can be measured by measuring the ratio of the height of a peak or peaks corresponding to Choline relative to the height of a peak or peaks of an internal standard. In a further embodiment, the amount of Choline can be measured by measuring the ratio of the area under a peak or peaks corresponding to Choline relative to the area under a peak or peaks of an internal standard.

Any suitable internal standard can be used. For example, the internal standard is total creatine when the MRS is based on $^1$H resonance, or internal standard is adenosine triphosphate (ATP) when the MRS is based on $^{31}$P resonance. The term "total creatine" refers to the combination of creatine and phosphocreatine. Creatine is buffered in cell systems; accordingly, the amount of creatine remains substantially constant. In accordance with this invention, the change in the amount of Choline measured as part of the early treatment response, e.g., within 168 hours or less, relates mainly, preferably only, to the change in the endomembranes.

It is contemplated that the present inventive method is applicable to monitoring early treatment response wherein the treatment involves any cytotoxic therapy.

In accordance with an embodiment of the present invention, inhibition of replication, transcription and/or translation causes an interruption in an up-regulated intracellular organelle; for example, an interruption in the function of the secretory granules and/or the transporting vesicles. In accordance with another embodiment of the invention, inhibition of the replication, transcription and/or translation causes an interruption in the function of the Golgi apparatus. In further embodiments of the invention, inhibition of the replication, transcription and/or translation causes an interruption in the function of the lysosomes, the endoplasmic reticulum, the mitochondrion, the nucleus, and/or the peroxisomes.

In accordance with the present invention, any suitable cancer or tumor can be treated, for example, a cancer selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, kidney cancer, and hepatocellular cancer.

In accordance with the present inventive method, early treatment response can be measured within a period of about 168 hours, preferably about 24 hours, and more preferably about 12 hours, of the treatment. For example, the response can be monitored every 12, 24, 36, 48, 60, 72, 84, 96, 108, 120, 132, 144, 156, or 168 hours, or any combination thereof, after administration of cytotoxic therapy.

Treatment response can also be documented using the current invention within 24 to 168 hours by monitoring protein translation. This embodiment utilizes a magnetic resonance magnet, equal to or greater than 1.5 Tesla, uses existing software and coils which are commercially available, has high spatial resolution, lacks radiation, employs user-friendly automatic sequences, allows non-invasive sequential analysis of drug doses/combinations, provides quantification from multi-sites, and can be employed with a plurality of drugs for trials. This embodiment can monitor treatment responses in vivo and in vitro, in humans and laboratory animals, as well as, in tissues and perfused cell extracts. This embodiment quantifies normal protein translation, as well as the amplified protein translation seen in cancer and cancer-related inflammation. Since protein translation occurs in all cells, all cancer histologies can be studied. This embodiment is applicable to cytostatic and cytotoxic drugs. Further, drugs augmenting protein translation can be monitored. Potential uses of this embodiment include, but are not limited to, drug development, detecting early cell kill and documenting the interruption of signaling pathways.

The present invention also provides a method for monitoring cancer treatment comprising: (a) localizing a tumor in a patient; (b) selecting a region of interest (ROI) of the tumor; (c) obtaining magnetic resonance spectra (MRS) of the ROI; (d) measuring the amount of Choline in the endomembranes from the MRS spectra; (e) initiating treatment comprising administering a cytotoxic therapy; (f) obtaining MR spectra of the tumor at the same ROI within a period of 7 days, preferably 3 days, and more preferably within 1 day, of initiating treatment; (g) measuring the amount of Choline in the endomembranes from the MR spectra; and (h) comparing the amount of Choline obtained before treatment with the amount of Choline obtained after treatment; whereby a decrease in the amount of Choline after treatment is indicative of a positive response to treatment.

The basis for clinical MR studies (e.g., MRS or MRI) is the one of the nuclei, for example, the hydrogen nucleus—the proton. The same machinery is used for these studies. They differ in the software manipulation of the emitted radiofrequency (RF) from the H nuclei. In MRI, the signal is used to create the image; in MRS, the signal is used to create the spectrum. Fourier Transform principle is the basis of the computer that allows the MRS software to separate the individual RFs within the signal. The spectrum therefore represents the different RFs being emitted within the selected region of interest (ROI). The points along the horizontal axis of the spectrum represent specific RFs emitted from each metabolite. The vertical axis of the spectrum is proportional to the amount of each metabolite forming the area beneath the RF peaks. Spectra can be obtained on 0.5 to 2.0T MR scanners, although high-field strength scanners provide better definition of the spectra. Spectra obtained with different-strength scanners can be compared on a scale in parts per million (ppm) along the horizontal axis because metabolites always reside at one or more specific sites, for example, alanine resides at 1.47, N-acetylaspartate resides at 2.0 and 2.6 ppm, creatine resides at 3.0 and 3.9 ppm, Choline resides at 3.2 ppm, and water resides at 5.0 ppm.

Any suitable MR spectrometer can be used in the practice of the present invention. Clinical MR spectra can be obtained on MR scanners, for example, utilizing the clinical spectroscopy package called proton brain exam/single voxel (PROBE/SV) developed by General Electric Medical Systems (Milwaukee, Wis.) for use with GE's 1.5 Tesla (T) MR scanner. See Norfray, J. et al., supra, and Norfray, J. F. et al., supra, for procedures for obtaining MR spectra, identification of the peaks corresponding to metabolites such as Choline, creatine, and others, and ratio of the peaks. See also Danielsen and Ross, *Magnetic Resonance Spectroscopy Diagnosis of Neurological Diseases*, Marcel Dekker, Inc. (1999); Ross, B. et al., *Magnetic Resonance Quarterly*, 10, 191-247 (1994); and Ross et al., U.S. Pat. No. 5,617,861. Based on the information in the above publications, as well as information available in the art, those of skill in the art should be able to practice the invention on all types of tumors in accordance with the present invention.

The present invention can be carried out in any suitable manner, for example, as follows. Prior to initiating a therapy on a patient, the tumor is localized. Thus, for example, magnetic resonance images (MRI's) of the tumor, e.g., brain metastasis, breast malignancy, or bone tumor, with axial, sagittal, and coronal T1 and T2 images are obtained with and without contrast. A region of interest (ROI) of tumor is selected. This can be carried out based on the MRI findings to determine the tumor volume and location to be studied. MR spectra of the ROI are obtained within the tumor utilizing short and/or long TE (echo time) pulse sequences. The spectra obtained are interpreted. The peak corresponding to Choline is identified, e.g., at a chemical shift of 3.22 ppm. Based on the Choline peak, the amount of total cellular membranes is determined from either the height of the peak or the area under the peak. An internal or external standard is identified in the ROI. An example of an internal standard is creatine or total creatine. An example of an external standard is 100% 2-(trimethylsilyl)ethanol (TSE), which may be taped to the head coil of the MR spectrometer. Kreis, R. et al., *J. Magnetic Resonance*, Series B 102, 9-19 (1993). The ratio of the Choline to the standard is calculated. The Choline to creatine ratio represents a measure of the total cell membranes within the ROI of the tumor prior to treatment.

The treatment of the tumor is initiated by administering an effective amount of cytotoxic agent starting from time zero. The early treatment response can be monitored, for example, at 24 hours (day 1) to 168 hours (day 7), as follows. The tumor is localized utilizing the same MRI pulse sequences as prior to the treatment. The same ROI is selected within the tumor. MR spectra of the tumor are obtained utilizing the same pulse sequences, the same TR (relaxation time), TE (echo time), phases, and frequency averages. The MR spectra are interpreted as before and the Choline to creatine ratios (e.g., height or area ratios) are calculated.

If the observed decrease in the Choline to creatine ratio is 15% or more, preferably 20% or more, and more preferably 25% or more relative to pre-treatment condition, then it can be concluded that an early response is positive and tumor regression is achieved. The early decrease in the Choline to creatine ratio identifies a decrease in the intracellular cell membranes, for example, a decrease in the organelles and their granules and/or vesicles. If the ratio of Choline to creatine increases, e.g., a 15% or more, preferably 20% or more, and more preferably 25% or more, of an early increase in the ratio is observed, the increase identifies an increase in the intracellular membranes, for example, an increase in the organelles and their granules and/or vesicles.

The use of MRS to follow cytotoxic therapy has one or more advantages. Coupling the amount endomembranes to the amount of protein synthesis provides a biomarker depicting meaningful biological activity. Membranes are composed of Choline molecules that can be visualized and quantified by MRS using any suitable nuclei, e.g., $^{31}P$, $^1H$, and $^{13}C$, preferably $^1H$. MRS measures the total choline. A decrease in the total choline documents failure of a cytotoxic therapy. Monitoring total choline is reproducible and allows quantification. The same pulse sequence by different manufacturers produces the same results allowing multi-site trials. The total choline biomarker end-point is more sensitive, and can be quantified compared to clinical end-points and MRI. It is believed that monitoring cytotoxic therapies by following endomembrane protein synthesis would have one or more of the following advantages improve patient outcome; change therapeutic choice; impact or diagnostic thinking; and impact on society.

The present invention further provides a method for determining effectiveness of cytotoxic therapy (a drug molecule or radiation) for treating cancer comprising administering the therapy (an amount of the molecule or radiation) to an animal having a cancerous tissue and measuring, by Magnetic Resonance Spectroscopy, the amount of Choline present in the cancerous tissue, particularly of the endomembranes, before and after administering the molecule, wherein the therapy comprises administration of a drug molecule or radiation cytotoxic therapy, whereby a decrease in the amount of Choline after administering the therapy is indicative of its effectiveness. The animals to be used in the present method can be, for example, mammals such as mice, rats, horses, guinea pigs, rabbits, dogs, cats, cows, pig, and monkeys. The amount of cytotoxic therapy will vary with a number of factors, e.g., weight of the animal, type of cancer, and severity of cancer, and is within the skill of the artisan. The potential cytotoxic drug can be administered by any suitable route of administration, e.g., oral, aerosol, parenteral, subcutaneous, intravenous, intraarterial, intramuscular, interperitoneal, rectal, and vaginal routes radiation can be hyperfractionated and/or accelerated. The cancer can be natural or induced. Thus, effectiveness of a cytotoxic therapy can be determined within a relatively short period of time, for example, within 12-168 hours, preferably 12-24 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for monitoring early treatment response of a cancer treatment in a patient comprising localizing a cancerous tissue in the patient, obtaining a Nuclear Magnetic Resonance (NMR) spectrum of the localized cancerous tissue, subjecting the patient to the cancer treatment, obtaining an NMR spectrum of the same tissue after subjecting the patient to the cancer treatment, wherein the NMR spectra are obtained by interrogating one or more nuclei selected from the group consisting of $^{31}P$, $^1H$, and $^{13}C$, and measuring from the NMR spectra the amount of Choline naturally present or formed in the endomembranes of the cancerous tissue before and after the cancer treatment, wherein said Choline is a metabolite of phospholipid metabolism occurring in the body of the cancer patient, wherein said cancer treatment comprises administration of cytotoxic therapy, whereby a decrease in the amount of Choline after treatment is indicative of a positive response.

2. The method of claim 1, wherein the NMR spectra are obtained by interrogating $^1$H.

3. The method of claim 1, wherein measuring the amount of Choline comprises measuring the height of a peak corresponding to Choline.

4. The method of claim 1, wherein measuring the amount of Choline comprises measuring the area under a peak corresponding to Choline.

5. The method of claim 1, wherein measuring the amount of Choline comprises measuring the ratio of the height of a peak corresponding to Choline relative to the height of peak of an internal standard.

6. The method of claim 5, wherein the internal standard is total creatine when the NMR spectra are obtained by interrogating $^1$H.

7. The method of claim 5, wherein the internal standard is adenosine triphosphate (ATP) when the NMR spectra are obtained by interrogating $^{31}$P.

8. The method of claim 1, wherein measuring the amount of Choline comprises measuring the ratio of the area under a peak corresponding to Choline relative to the area under a peak of an internal standard.

9. The method of claim 8, wherein the NMR spectra are obtained by interrogating $^1$H and the internal standard is total creatine.

10. The method of claim 1, wherein the cytotoxic therapy is radiation and/or chemotherapy.

11. The method of claim 1, wherein measuring the amount of Choline comprises measuring the amount of choline, phosphocholine, phosphatidylcholine, lysophosphatidylcholine, glycerophosphocholine, phosphomonoesters of choline, phosphodiesters of choline, phosphoethanolamine, glycerophosphoethanolamine, or any combination thereof.

12. The method of claim 1, wherein the amount of Choline is measured by obtaining an NMR spectrum within a period of about 168 hours of said treatment.

13. The method of claim 12, wherein the amount of Choline is measured by obtaining an NMR spectrum within a period of about 24 hours.

14. The method of claim 13, wherein the amount of Choline is measured by obtaining an NMR spectrum within 12 hours of said treatment.

15. The method of claim 1, wherein the cytotoxic therapy is radiation and/or chemotherapy.

16. The method of claim 1, wherein the cancer is selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, and hepatocellular cancer.

17. The method of claim 1, wherein cytotoxic therapy causes an interruption in an up-regulated intracellular organelle.

18. The method of claim 17, wherein the interruption in the up-regulated intracellular organelle takes place in the secretory granules.

19. The method of claim 17, wherein the interruption in the up-regulated intracellular organelle takes place in the transporting vesicles.

20. The method of claim 1, wherein inhibition of replication, transcription and/or translation causes an interruption in a function of the Golgi apparatus.

21. The method of claim 1, wherein inhibition of replication, transcription and/or translation causes an interruption in a function of the lysosomes.

22. The method of claim 1, wherein inhibition of replication, transcription and/or translation causes an interruption in a function of the endoplasmic reticulum.

23. The method of claim 1, wherein inhibition of replication, transcription and/or translation causes an interruption in a function of the mitochondrion.

24. The method of claim 1, wherein inhibition of replication, transcription and/or translation causes an interruption in a function of the nucleus.

25. The method of claim 1, wherein inhibition of replication, transcription and/or translation causes an interruption in a function of the peroxisomes.

26. A method for monitoring cancer treatment in a patient comprising:
(a) localizing a tumor in the patient; (b) selecting a region of interest (ROI) of the tumor; (c) obtaining a nuclear magnetic resonance (NMR) spectrum of the ROI; (d) measuring from the NMR spectrum the amount of Choline naturally present or formed in the endomembranes, wherein said Choline is a metabolite of phospholipid metabolism occurring in the body of the cancer patient; (e) initiating treatment comprising administering a cytotoxic therapy to the patient; (f) obtaining an NMR spectrum of the tumor at the same ROI within a period of 7 days of initiating treatment; (g) measuring the amount of Choline present in the endomembranes from the NMR spectrum obtained after initiating the treatment; and (h) comparing the amount of Choline obtained before treatment with the amount of Choline obtained after initiating treatment; whereby a decrease in the amount of Choline after treatment is indicative of a positive response to treatment.

27. The method of claim 26, wherein the NMR spectrum of the tumor is obtained within 3 days of initiating treatment.

28. The method of claim 27, wherein the NMR spectrum of the tumor is obtained within 1 day of initiating treatment.

29. A method for determining effectiveness of a molecule as a drug, or radiation, for treating cancer in an animal comprising localizing a cancerous tissue in the animal, obtaining an NMR spectrum of the localized cancerous tissue, subjecting the animal to the treatment, obtaining an NMR spectrum of the same tissue after subjecting the animal to the treatment comprising administering the molecule or radiation, wherein the NMR spectra are obtained by interrogating one or more nuclei selected from the group consisting of $^{31}$P, $^1$H, and $^{13}$C, and measuring from the NMR spectra the amount of Choline naturally present or formed in the endomembranes of the cancerous tissue before and after the treatment, wherein said Choline is a metabolite of phospholipid metabolism occurring in the body of the animal, wherein said molecule or radiation comprises a cytotoxic agent, whereby a decrease in the amount of Choline after administering molecule or radiation is indicative of its effectiveness.

30. A method for monitoring protein translation in an animal afflicted with cancer comprising localizing a cancerous tissue in the animal, obtaining an NMR spectrum of the localized cancerous tissue, subjecting the animal to a cancer treatment comprising administering a molecule or radiation, obtaining an NMR spectrum of the same tissue after subjecting the animal to the treatment, wherein the NMR spectra are obtained by interrogating one or more nuclei selected from the group consisting of $^{31}$P, $^1$H, and $^{13}$C, and measuring from the NMR spectra the amount of Choline naturally present or formed in the endomembranes of the cancerous tissue before and after administering the molecule or radiation, wherein said Choline is a metabolite of phospholipid metabolism and results from organellar protein synthesis occurring in the body of the animal.

\* \* \* \* \*